(12) United States Patent
Scovel

(10) Patent No.: US 6,635,038 B2
(45) Date of Patent: Oct. 21, 2003

(54) DISPOSABLE INCONTINENCE DEVICE

(76) Inventor: Aldrene K Scovel, P.O. Box 741, Koloa, HI (US) 96756

( * ) Notice: Subject to any disclaimer, the term of this patent is extended or adjusted under 35 U.S.C. 154(b) by 0 days.

(21) Appl. No.: 09/827,884

(22) Filed: Apr. 6, 2001

(65) Prior Publication Data

US 2002/0177825 A1 Nov. 28, 2002

(51) Int. Cl.$^7$ .............................. A61F 5/44; A61F 13/15
(52) U.S. Cl. ....................... 604/353; 604/347; 604/351; 604/385.03; 604/385.09; 604/385.01
(58) Field of Search ................................. 604/353, 317, 604/319, 338, 339, 349, 351, 385.13, 385.03, 385.09, 385.24, 392, 327, 340–347, 389.19; 602/67–73; 2/403, 405

(56) References Cited

U.S. PATENT DOCUMENTS

| | | |
|---|---|---|
| 22,293 A | 12/1858 | Jensen |
| 741,173 A | 10/1903 | Seidel |
| 2,024,341 A | 12/1935 | De Graff |
| 2,439,683 A * | 4/1948 | Broderick .................... 604/353 |
| 2,484,356 A * | 10/1949 | Ribeiro et al. .............. 604/347 |
| 2,864,369 A | 12/1958 | Morrow |
| 3,032,038 A | 5/1962 | Swinn |
| 3,517,666 A | 6/1970 | Atlee |
| 3,707,969 A | 1/1973 | Sanford |
| 4,200,102 A * | 4/1980 | Duhamel et al. ........... 604/331 |
| 4,564,956 A * | 1/1986 | DiBuono ......................... 2/16 |
| 4,590,931 A * | 5/1986 | Kidwell, Jr. ................. 602/70 |
| 4,601,716 A | 7/1986 | Smith |
| 4,813,943 A * | 3/1989 | Smith ........................... 604/329 |
| 4,886,510 A * | 12/1989 | Matsuura ..................... 604/353 |
| 5,009,649 A | 4/1991 | Goulter et al. |
| 5,207,233 A * | 5/1993 | Barnes ......................... 128/842 |
| 5,275,592 A | 1/1994 | Grizzaffi |
| 5,406,649 A * | 4/1995 | Bolembach ..................... 2/158 |
| 5,649,913 A * | 7/1997 | Cohen ............................ 2/401 |
| 5,735,837 A * | 4/1998 | Ishikawa ................ 604/385.09 |
| 5,855,206 A * | 1/1999 | Ireland ......................... 128/844 |
| 5,984,910 A * | 11/1999 | Berke .......................... 604/352 |
| 6,010,489 A * | 1/2000 | Blackburn ................... 604/349 |
| 6,059,762 A | 5/2000 | Boyer et al. |
| 6,113,582 A * | 9/2000 | Dwork ........................ 604/349 |
| 6,132,412 A | 10/2000 | Jones |
| 6,152,903 A * | 11/2000 | Falconer ..................... 604/317 |
| 6,197,011 B1 * | 3/2001 | Freitas et al. ........... 604/385.03 |
| 6,390,886 B1 * | 5/2002 | Roberts ........................ 450/37 |
| 6,443,930 B1 * | 9/2002 | Silverstein .................. 604/353 |

\* cited by examiner

*Primary Examiner*—Henry Bennett
*Assistant Examiner*—Kathryn Ferko
(74) *Attorney, Agent, or Firm*—Michael I Kroll (57) ABSTRACT

The present invention 10 discloses an incontinence device having a disposable urinary bag 18 having a plurality of attachment means 22 located on its outside surface for securement of the disposable urinary bag 18 to the adjustable attachment belt 14. Housed within the disposable urinary bag 18 is an absorbent material 34 for urine absorption. The disposable urinary bag 18 also has in its upper central region an elastic ring or seal 24 that provides a barrier against urine when a penis 36 is inserted into it. On the top portion of the elastic ring 24, a slit 28 is provided in conjunction with a sealing tab 26 with adhesive 32 to enlarge or constrict the size of the elastic ring 24. The adjustable attachment belt 14 is comprised of a portion that fits around the wearer's waist with a plurality of attachment means to secure the upper portion of the disposable urinary bag in conjunction with a plurality of leg straps 16 to provide connection means from the adjustable attachment belt 14 to the lower portion of the disposable urinary bag 18.

1 Claim, 9 Drawing Sheets

DISPOSABLE INCONTINENCE DEVICE

BACKGROUND OF THE INVENTION

1. Field of the Invention

The present invention relates generally to an incontinence device and, more specifically, to a disposable urinary bag outfitted to accommodate a male's anatomy that may be used without, or in conjunction with an adjustable attachment belt. The disposable urinary bag has a plurality of attachment means located on its outside surface for securement of the disposable urinary bag to the adjustable attachment belt. Housed within the disposable urinary bag is an absorbent material for urine absorption. The disposable urinary bag also has in its upper central region an elastic ring that provides a barrier against urine when a penis is inserted into it. On the top portion of the elastic ring, a slit is provided in conjunction to a sealing tab with adhesive to enlarge or constrict the size of the elastic ring. The adjustable attachment belt is comprised of a circular portion that fits around the wearers waist with a plurality of attachment means to secure the upper portion of the disposable urinary bag in conjunction with a plurality of leg straps to provide connection means from the adjustable attachment belt to the lower portion of the disposable urinary bag.

2. Description of the Prior Art

There are other incontinence devices designed for the containment of urine. Typical of these is U.S. Pat. No. 22,293 issued to N. Jensen on Dec. 14, 1858.

Another patent was issued to J. Seidel on Oct. 13, 1903 as U.S. Pat. No. 741,173. Yet another U.S. Pat. No. 2,024,341 was issued to G. C. De Graff on Dec. 17, 1935 and still yet another was issued on May 1, 1962 to M. A. Swinn as U.S. Pat. No. 3,032,038.

Another patent was issued to Mable M. Sanford on Jan. 2, 1973 as U.S. Pat. No. 3,707,969. Yet another U.S. Pat. No. 4,601,716 was issued to Lonnie W. Smith on Jul. 22, 1986. Another was issued to Victor Goulter on Apr. 23, 1991 as U.S. Pat. No. 5,009,649 and still yet another was issued on Jan. 4, 1994 to Eugenia Grizzaffi as U.S. Pat. No. 5,275,592.

Another patent was issued to Mildred E. Boyer on May 9, 2000 as U.S. Pat. No. 6,059,762. Yet another U.S. Pat. No. 6,132,412 was issued to Rosemary N. Jones on U.S. Pat. No. 6,132,412.

U.S. Pat. No. 22,293
Inventor: N. Jensen
Issued: Dec. 14, 1858

Forming instruments of two wire springs a and g, the springs g, which supports the bag, being hinged and hooked to the other spring a, for the purposes as set forth.

U.S. Pat. No. 741,173
Inventor: J. Seadel
Issued: Oct. 13, 1903

A sanitary urinal, comprising a water-tight flexible bag having an open mouth, an encircling string runway in the bag near its mouth, oppositely-drawing gathering-strings in the runway, a flap member of considerable width secured to the bag at the front and extending from the open end thereof in the direction of the length of the bag and provided at its free end with a transverse belt runway, and a belt in the runway adapted to pass around the body of a person above the hips and secure the bag to the person.

U.S. Pat. No. 2,024,341
Inventor: G. C. Graff
Issued: Dec. 17, 1935

A urinary receptacle for male patients, comprising a suspensory, a relatively soft flexible fabric apron forming a part of the front of the suspensory, a flexible water proof bag having its front and back substantially flat and adjacent each other, the back being secured to said apron and the top of the bag adapted to be opened, said apron and back of said bag being formed with an opening near the center of the bag, absorbent material inserted through the top of the bag to partially distend the bag and absorb liquid in the bag to thereby prevent the liquid from escaping if the bag should be inverted, said bag and the absorbent material having sufficient rigidity to normally lie in relatively flat form against the users lags and to prevent the bag from entering between the patients legs.

U.S. Pat. No. 2,864,369
Inventor: T. F. Morrow
Issued: Apr. 2, 1956

A urine bag for a male person, comprising an open-topped bag receptacle constructed of a continuous sheet of pliable rubber and being formed to converge inwardly and downwardly from the open top whereby the largest transverse area of the bag interior is at the open top, said bag receptacle having a smooth and continuous upper edge with a forward portion and a rear portion, said forward portion being disposed well above the rear portion of the upper edge, said bag receptacle having at least one substantially continuous inwardly projecting sealing flange adjacent the upper edge and extending around the bag, the forward portion of the upper edge and the sealing flange sealingly engaging and fitting the lower abdominal portions of the person immediately above the genitals and the lower rear portion of the upper edge of the sealing flange sealingly engaging and fitting the body portions adjacent to and behind the scrotum, whereby to prevent flow of liquid out of the bag receptacle, the bag having a plurality of minute air vents apertures positioned below the forward portions of the upper edge to be positioned in confronting relation with the lower abdominal body portions above the genitals, and means secured to an integral portion of the bag receptacle adjacent the upper edge forward portion and constructed and arranged for securing the bag receptacle to the person's body U.S. Pat. No. 3,032,038
Inventor: M. A. Swinn
Issued: May 1, 1962

A male urinal comprising in combination, a body encircling belt, a pair of leg straps connected at one end to the belt slightly to the rear of the side median, a pair of buckles attached to the front of the body encircling belt adjacent to the respective side median, the free ends of the leg strap adapted to pass through the crotch of a wearer and adjustably engage the buckles, a roll on type organ accommodating receptacle, a connecting member on each leg strap including a loop on one end snugly embracing the leg strap so that it is adjustable there along in frictional gripping relation, means embracing the organ accommodating receptacle adjacent its upper end and co-acting with the free ends of the connecting members to secure the upper end of the organ accommodating receptacle in intimate relation with the wearer of the urinal.

U.S. Pat. No. 3,517,666
Inventor: j. S. Atlee
Issued: May 25, 1966

A man's undergarment comprising a body encircling member including a waist band and front and back portions, a pouch to receive, cover and accommodate the genitals with substantially no restriction or support there of, said pouch including an upper edge, a rear edge and inner edges between them, means joining said upper edge of said pouch to said front portion of said body member, and means joining said rear edge of said pouch to said back portion of said body member through the wearer's crotch, said pouch being of such size and shape that, as normally disposed on a standing man, it provided a vertically orientated front which is disposed beyond the forward extremities of the wearer's normally disposed genitals with said inner edges disposed along and normally in contact with the wearer's crotch and lower groins.

U.S. Pat. No. 3,707,969
Inventor: Mable M. Sanford
Issued: Jan. 2, 1973

An incontinence device formed from an elongated sheet of flexible planer, waterproof material having a front panel, an intermediate panel, and a rear panel. The front panel is formed to extend over the pubic area between the furrows of the groin, and the rear buttocks, while the intermediate panel is formed to extend from the front panel, between the legs, to the rear panel and to form a receptacle for moisture absorbent material and to receive the genital organs. The sheet is gathered to an elastic strip along its edges that extend between the front panel and rear panel to provide yieldable expansion.

The intermediate panel is folded along the lines extending generally longitudinally of the sheet in a direction away from the front panel to provide pleat like walls that are expandable transversely of the sheet for the genital organs and moisture absorbent material, and a relatively wide transversely extending pleat extending between the side edges of the intermediate panel provides a pair of opposed walls defining opposite sides of a forwardly opening recess to receive and restrict rearward flow of moisture within the forward portion of the receptacle toward the rear panel.

The front panel is held in position by elastic bands releasably secured thereto and to the rear panel, to releasably hold the device in position, and to permit forward dropping of the panel to remove moisture laden material and to enable replacement without removal of the device.

U.S. Pat. No. 4,601,716
Inventor: Lonnie W. Smith
Issued: Jul. 22, 1986

There is disclosed a sanitary disposable sheath intended for wearing on the penis of males which is formed with a moisture absorbent pad to absorb excretions and urine. The sheath is intended for use by normal, healthy males and not as a prosthetic device, and a method of use is also disclosed and claimed. Preferably, the sheath is formed as a laminate of an outer moisture resistant sheath and an inner, coextensive, moisture permeable liner, with an intermediate moisture absorbent pad. The sheath is provided with either an elastic band closure about its neck, or Velcro type fabric attachment bands to retain it distally on a penis.

U.S. Pat. No. 5,009,649
Inventor: Victor Goulter
Issued: Apr. 23, 1991

A male incontinence device comprises a condom (16) which fits over the end of a penis (17) and is secured by a band (11) having overlapping ends with H&L fasteners. When the condom is filled with a quantity of urine, it can be removed and emptied. Alternatively, the distal end of the condom has a valve (12, 13) thereat for manual emptying of the condom when it is in place. The valve may comprise a tubular housing (12) fitted into an end of the condom and a plug (3) which can be removably inserted into the housing. A brief-type undergarment (32) has a pouch 33 for supporting the condom when filled with urine (37). In lieu of a separate housing, the end of the condom may be thickened and formed into a tube (41) so that a plug (43) can be inserted into the tube. Alternatively, the end of the condom can be fitted with a ball-obturator valve (47, 49, 50) which can be opened to empty the condom by squeezing it from outside to distort the valve seat and thus open the seal formed by the ball obturator.

U.S. Pat. No. 5,275,592
Inventor: Eugenia Grizzaffi
Issued: Jan. 4, 1994

A device for incontinent males includes an athletic supporter having a pocket and a disposable insert which fits into the pocket. The athletic supporter includes a waistband which fits around the waist of a user of the device and which helps to hold the pocket adjacent the penis of the user. The disposable insert which is placed in the pocket of the athletic supporter is substantially cylindrical and sized to be received in the pocket of the athletic supporter includes a layer of absorbent material, a waterproof material on the exterior of the layer of absorbent material, and a cavity sized to receive a human penis. The layer of absorbent material preferably includes a first portion which surrounds the cavity and a second portion which extends between the cavity and the second, closed end of the insert, the second portion having a length of between one half and three quarters of the distance between the first, open end of the insert and the second, closed end of the insert. The insert preferably also includes an inner liner which separates the user's penis from the layer of absorbent material so that moisture in the absorbent layer does not come into contact with the user's skin.

U.S. Pat. No. 6,059,762
Inventor: Mildred E. Boyer
Issued: May 9, 2000

A urinary incontinence device comprises a cover portion for male genitalia and a separable urine-collecting pouch. The cover portion has a frontal penis opening therethrough, a strap member encircling the wearer's body and securing the cover potion to the genitalia, a separate liquid-impervious pouch having an open, and means for removably attached the neck portion to the cover portion to enable a penis protruding through the cover portion opening to enter into the pouch. The pouch contains a liquid-absorbent media for suspension of liquid by the media, and preferably has a zipper lock on the side of the pouch opposite the cover portion opening to enable an active male to open the zipper and extend his penis therethrough for discharge of urine into a urinary receptacle.

U.S. Pat. No. 6,132,412
Inventor: Rosemary N. Jones
Issued: Oct. 17, 2000

This invention relates generally to a disposable type of covering or shield, which primarily is contoured and for use in conjunction with the male, and to provide a covering device for use for overlying the male anatomy, and to provide for elimination of urinary discharges, particularly amongst elderly patients, or the male who is incontinent.

While these incontinence devices suitable for the purposes for which they were designed, they would not be as suitable for the purposes of the present invention, as hereinafter described.

SUMMARY OF THE PRESENT INVENTION

The present invention discloses an incontinence device having a disposable urinary bag having a plurality of attachment means located on its outside surface for securement of the disposable urinary bag to the adjustable attachment belt. Housed within the disposable urinary bag is an absorbent material for urine absorption. The disposable urinary bag also has in its upper central region an elastic ring or seal that provides a barrier against urine when a penis is inserted into it. On the top portion of the elastic ring, a slit is provided in conjunction with a sealing tab with adhesive to enlarge or constrict the size of the elastic ring. The adjustable attachment belt is comprised of a portion that fits around the wearer's waist with a plurality of attachment means to secure the upper portion of the disposable urinary bag in conjunction with a plurality of leg straps to provide connection means from the adjustable attachment belt to the lower portion of the disposable urinary bag.

A primary object of the present invention is to provide an incontinence device made to accommodate a males anatomy.

Another object of the present invention is to provide an incontinence device with a disposable urinary bag.

Yet another object of the present invention is to provide an incontinence device in which the disposable urinary bag is held to the wearer via an adjustable attachment belt and leg straps.

Still yet another object of the present invention is to provide an incontinence device with an elastic ring to from a seal around the penis.

Yet another object of the present invention is to provide an incontinence device with a slit and sealing tab on the elastic ring for size adjustment.

Additional objects of the present invention will appear as the description proceeds.

The present invention overcomes the shortcomings of the prior art by providing an incontinence device formed to accommodate a males anatomy with a disposable urinary bag that attaches to the wearer by means of a adjustable attachment belt and a plurality of leg straps. Also by providing an elastic ring on the disposable urinary bag that is outfitted with an elastic ring with a slit and sealing tab to accommodate different size penises.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

With regard to reference numerals used, the following numbering is used throughout the drawings.

10 present invention
12 user
14 waist attachment belt
15 front strap
16 leg strap
17 upper attachment
18 bag
19 lower attachment
20 belt adjustment means
22 hook and loop material
24 elastic ring
26 sealing tab
28 slit
30 flaps
32 fastening means
34 absorbent material
36 penis
38 impermeable layer
40 edge of slit
42 front wall
44 rear wall

DESCRIPTION OF THE PREFERRED EMBODIMENT(S)

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
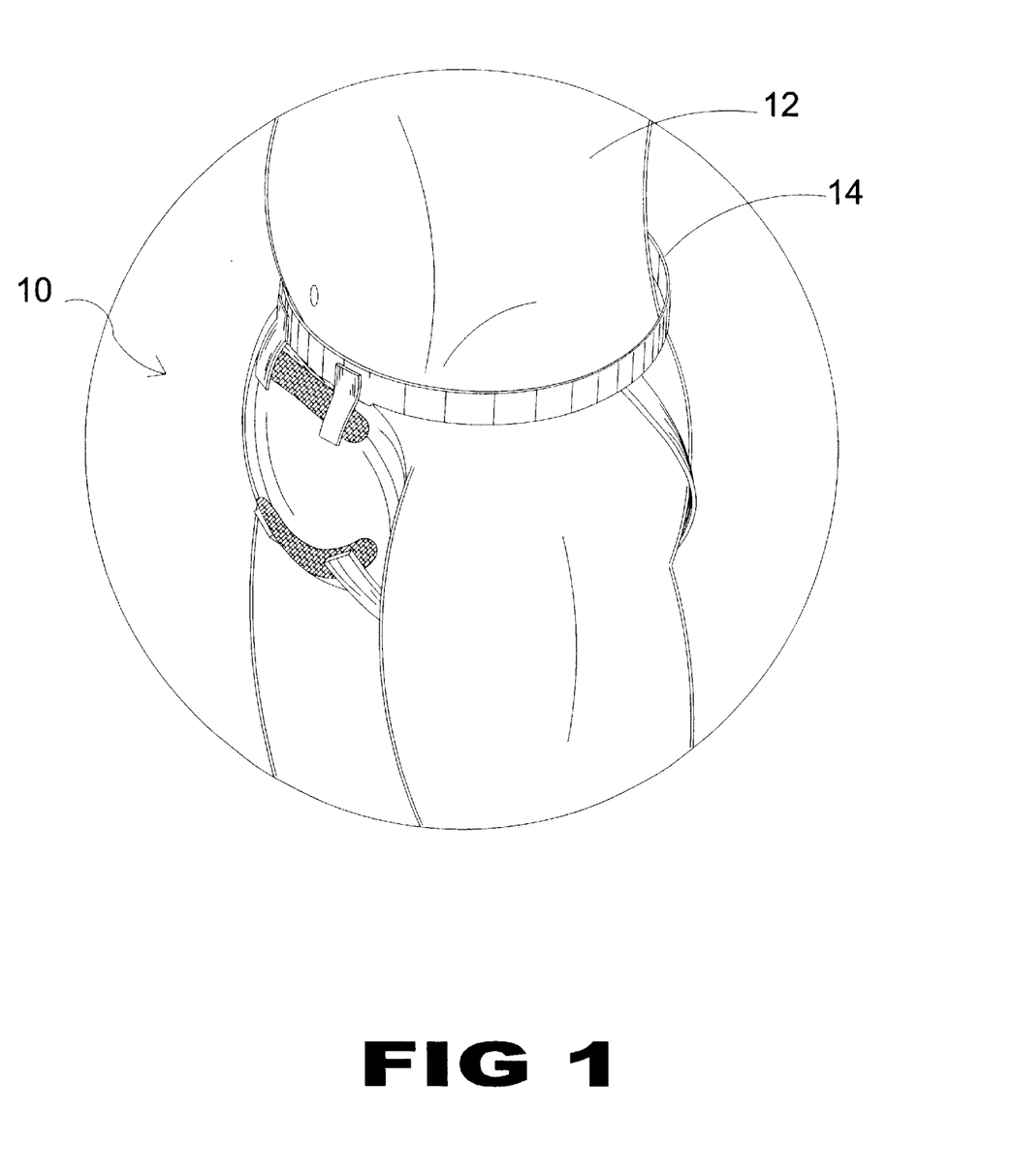
FIG. 1 is a perspective view of the present invention.

Turning to FIG. 1, shown therein is a perspective view of the present invention 10 showing the present invention being held in place about a user 12 using an adjustable waist attachment belt 14 worn about the waist of the user 12.

Figure 2:
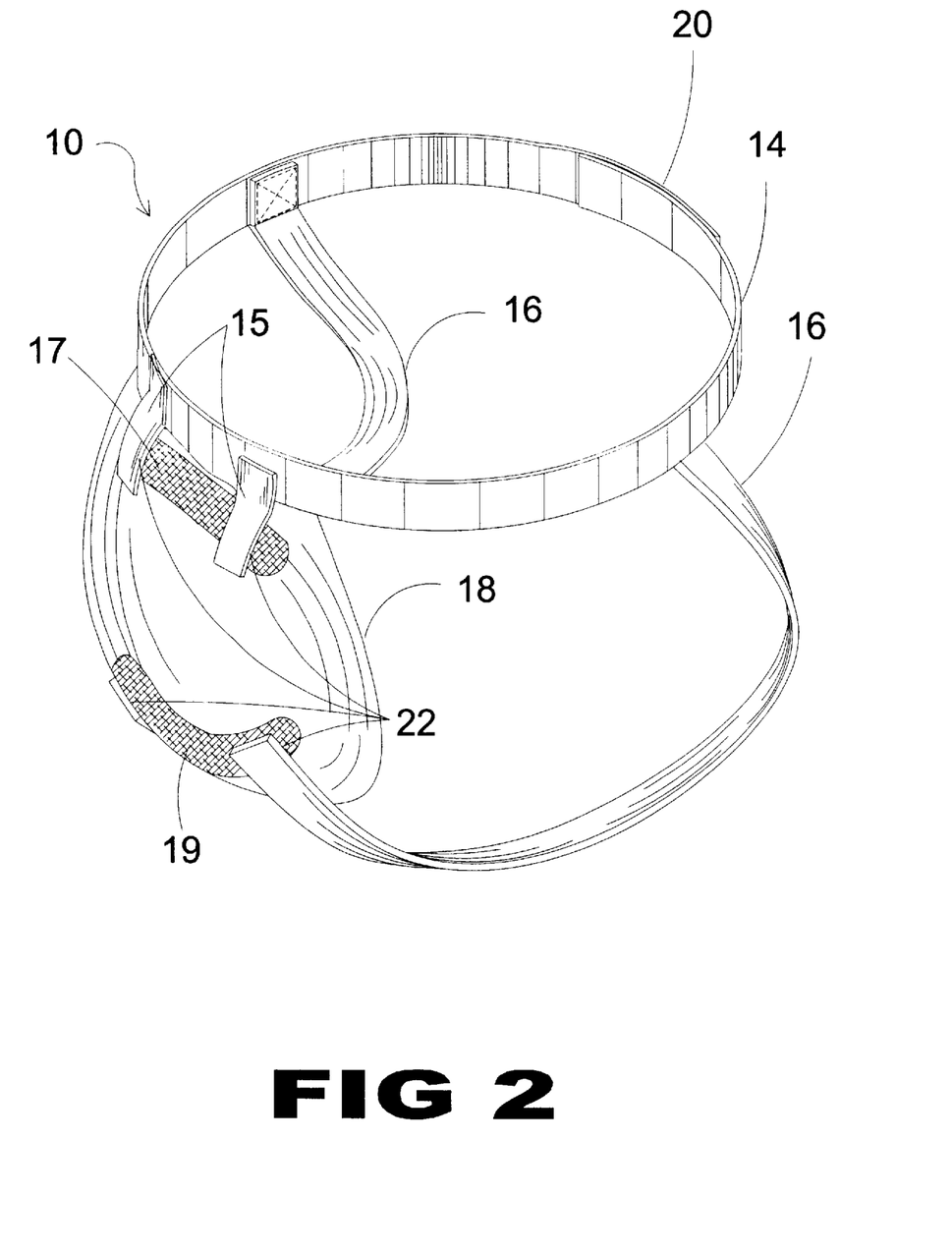
FIG. 2 is an isometric view of the present invention.

Turning to FIG. 2, shown therein is an isometric view of the present invention 10 showing the present invention having a plurality of leg straps 16 extending from waist belt 14 to the urinary bag 18 to secure the lower portion of the disposable urinary bag 18 in between the user's legs when in use. Also shown is the waist belt 14 with an adjustment means 20 along with upper 17 and lower 19 mating hook and loop material 22 for attaching leg straps 16 to the present invention 10. Front straps 15 for supporting the urinary bag 18 are also shown.

Figure 3:
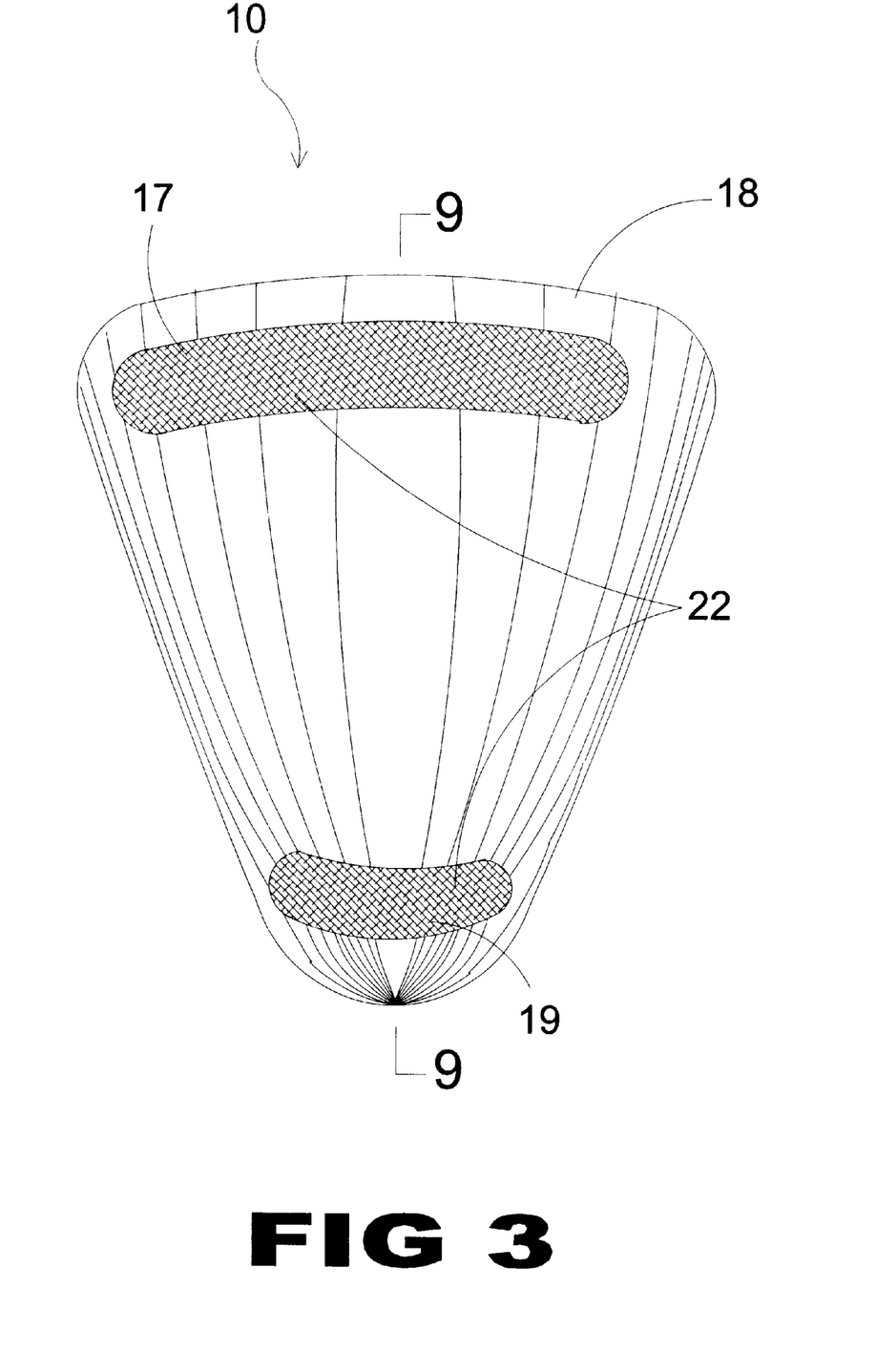
FIG. 3 is a front view of the present invention.

Turning to FIG. 3, shown therein is a front view of the present invention 10 showing the present invention having a plurality of attachment means 22 being an upper 17 and lower 19 attachment to enable the disposable urinary bag 18 to be attached to the adjustable attachment belt and leg straps.

Figure 4:
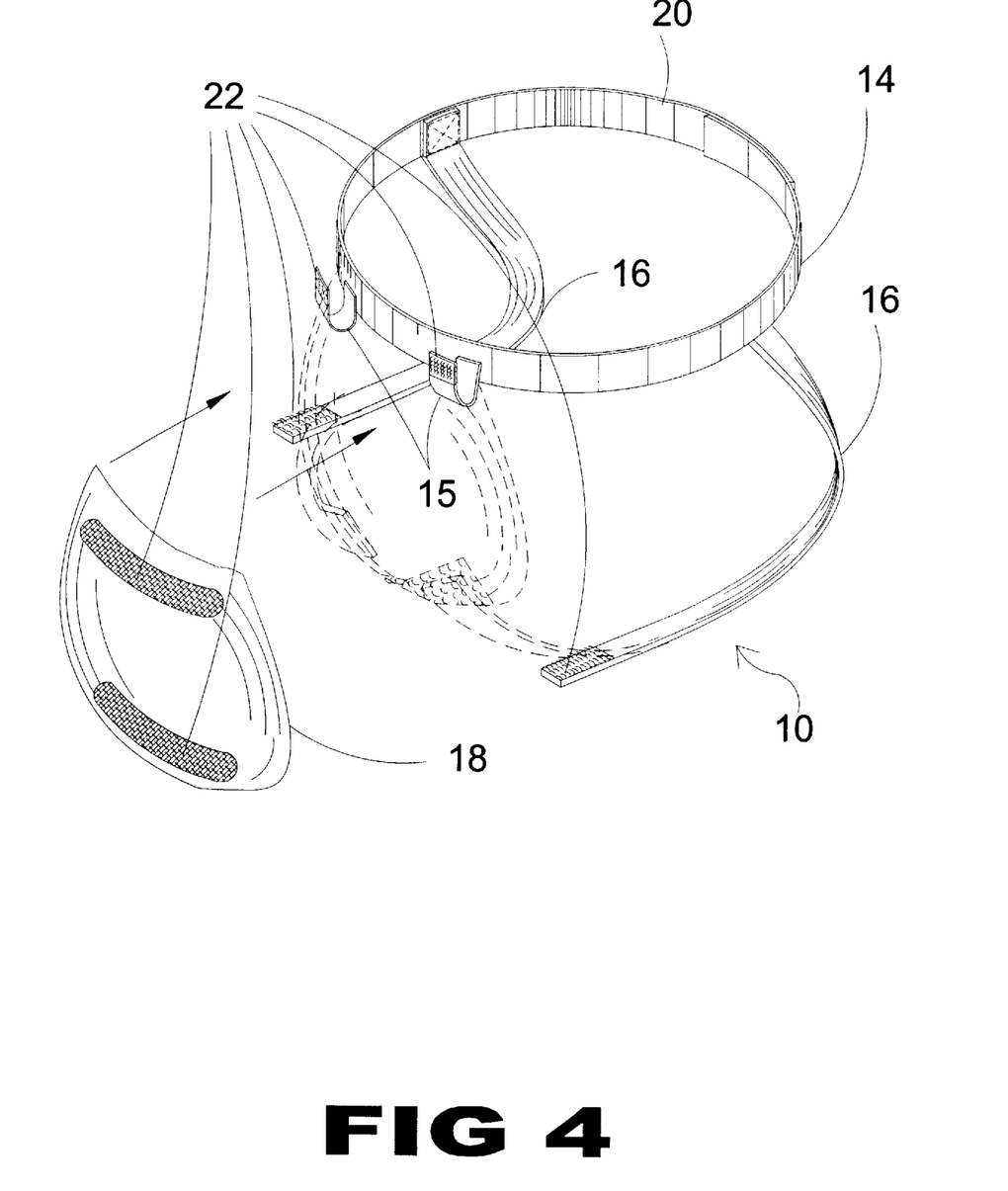
FIG. 4 is an isometric view of the present invention.

Turning to FIG. 4, shown therein is an isometric view of the present invention 10 showing the attachment of the disposable urinary bag 18 to the adjustable attachment belt 14 and leg straps 16 via a plurality of attachment means 22 including front straps 15 located on the disposable urinary bag 18, the front of the attachment belt 14 and ends of the leg straps 16. Belt adjustment means 20 is also shown.

Figure 5:
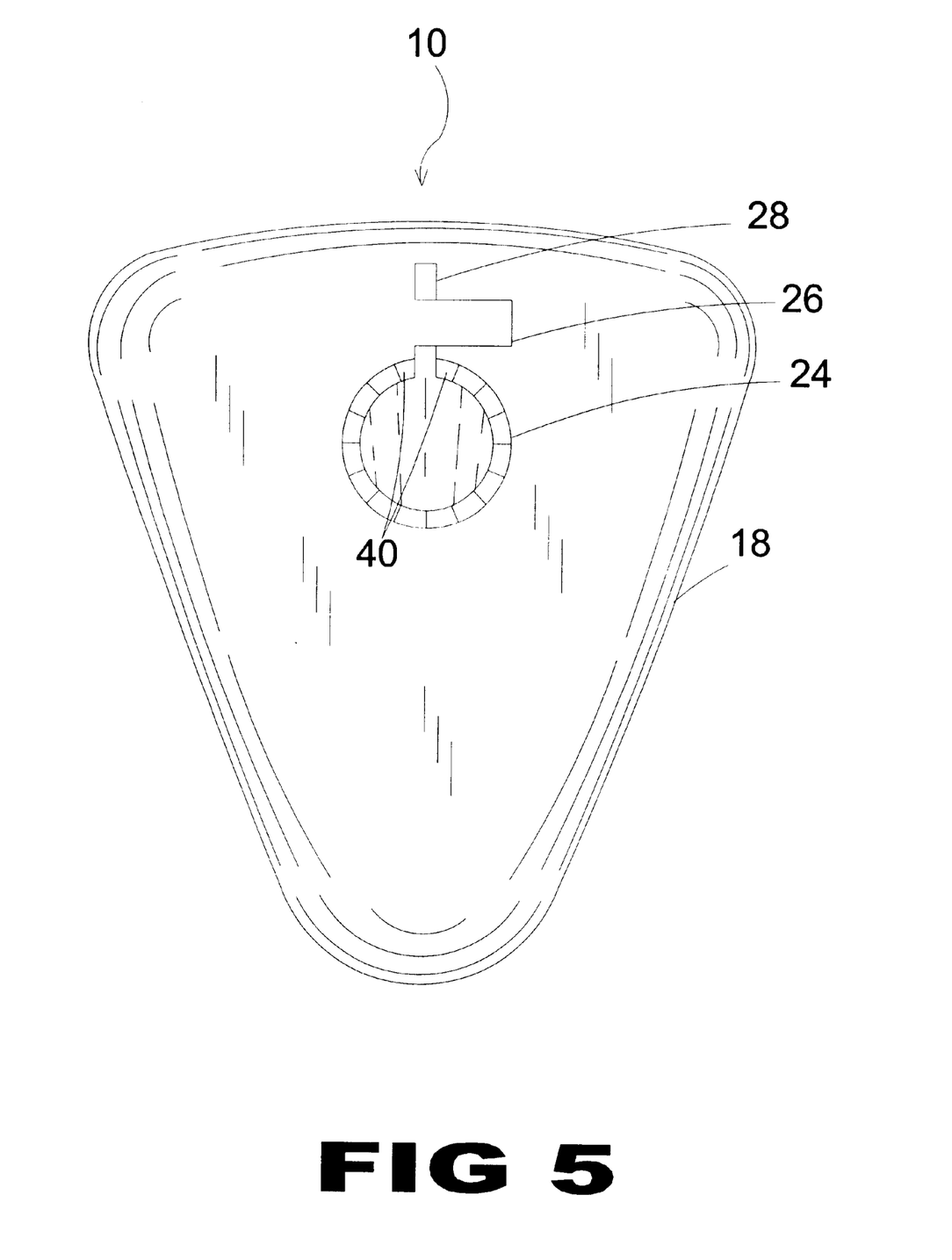
FIG. 5 is a back view of the present invention.

Turning to FIG. 5, shown therein is a back view or inside view of the present invention 10 showing the present invention having an elastic ring or seal 24 in its upper central region to expand and contract around a penis (not shown but see FIG. 9) to form a seal around it to prevent spillage of urine. Also shown are the bag 18, sealing tab 26 and slit 28.

Figure 6:
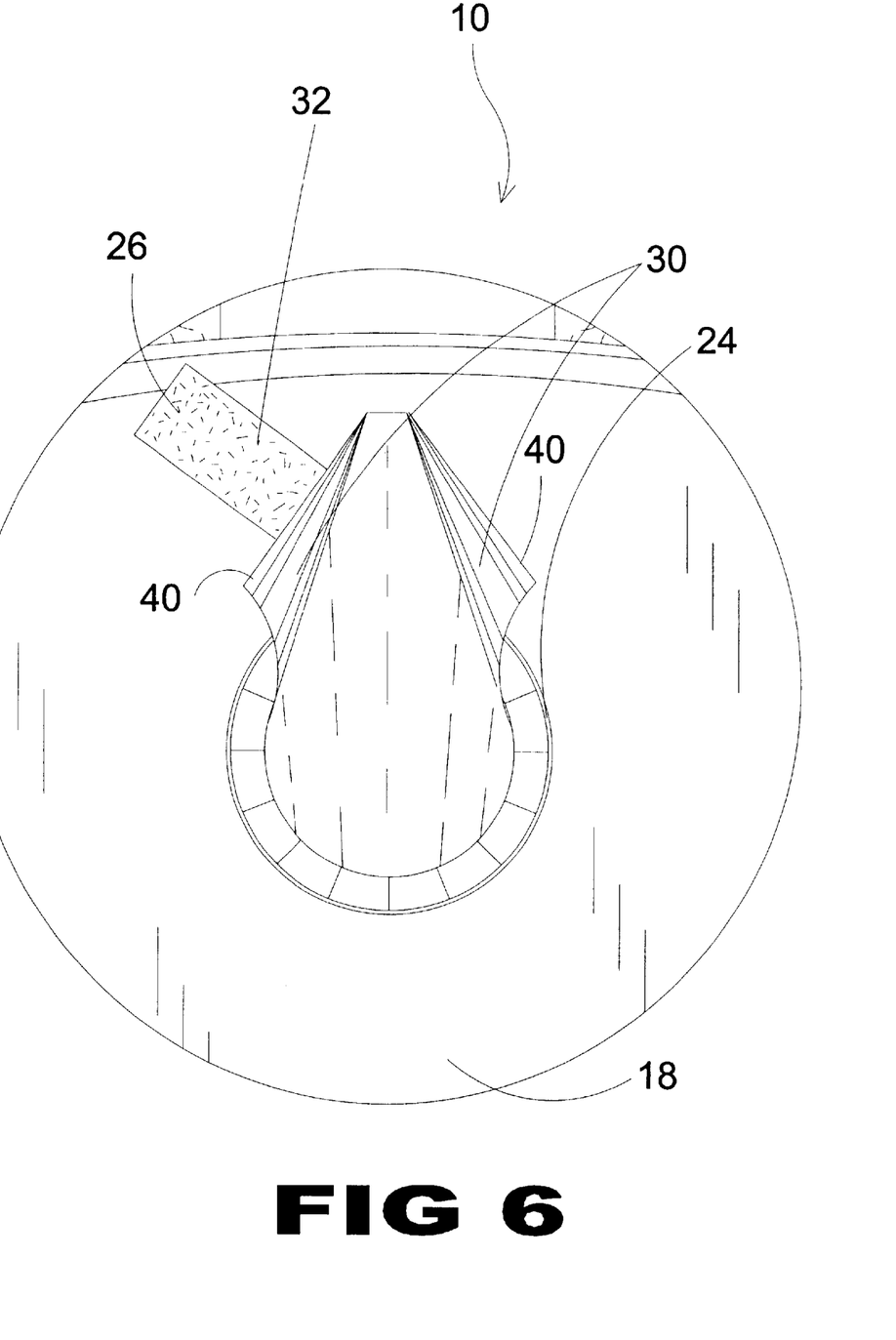
FIG. 6 is a back view of the present invention.

Turning to FIG. 6, shown therein is a back view of the present invention showing the present invention 10 in the receiving position with the edges 40 of the slit folded back into folds, after first releasing sealing tab 26, to allow easier insertion of a penis into the elastic ring 24. Shown are the spread apart slit edges 40 to form flaps 30 and sealing tab fastening means 32 being, e.g., adhesive, hook and loop material 22 or the like.

Figure 7:
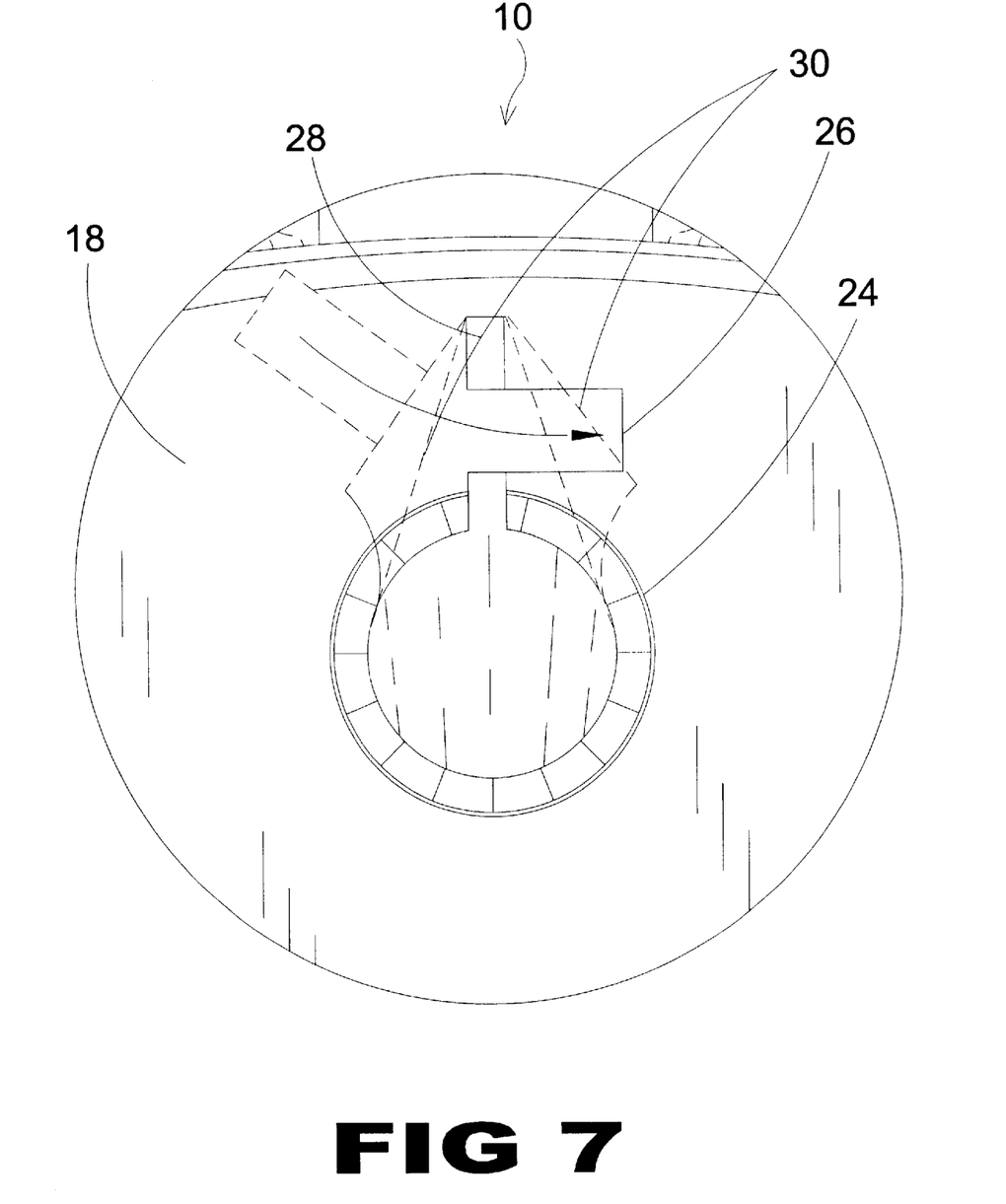
FIG. 7 is a back view of the present invention.

Turning to FIG. 7, shown therein is a back view of the present invention 10 showing the transition of the elastic ring 24 from the receiving position of FIG. 6 to the sealed position via pulling the sealing tab 26 over the flaps 30. The bag 18 is also shown.

Figure 8:
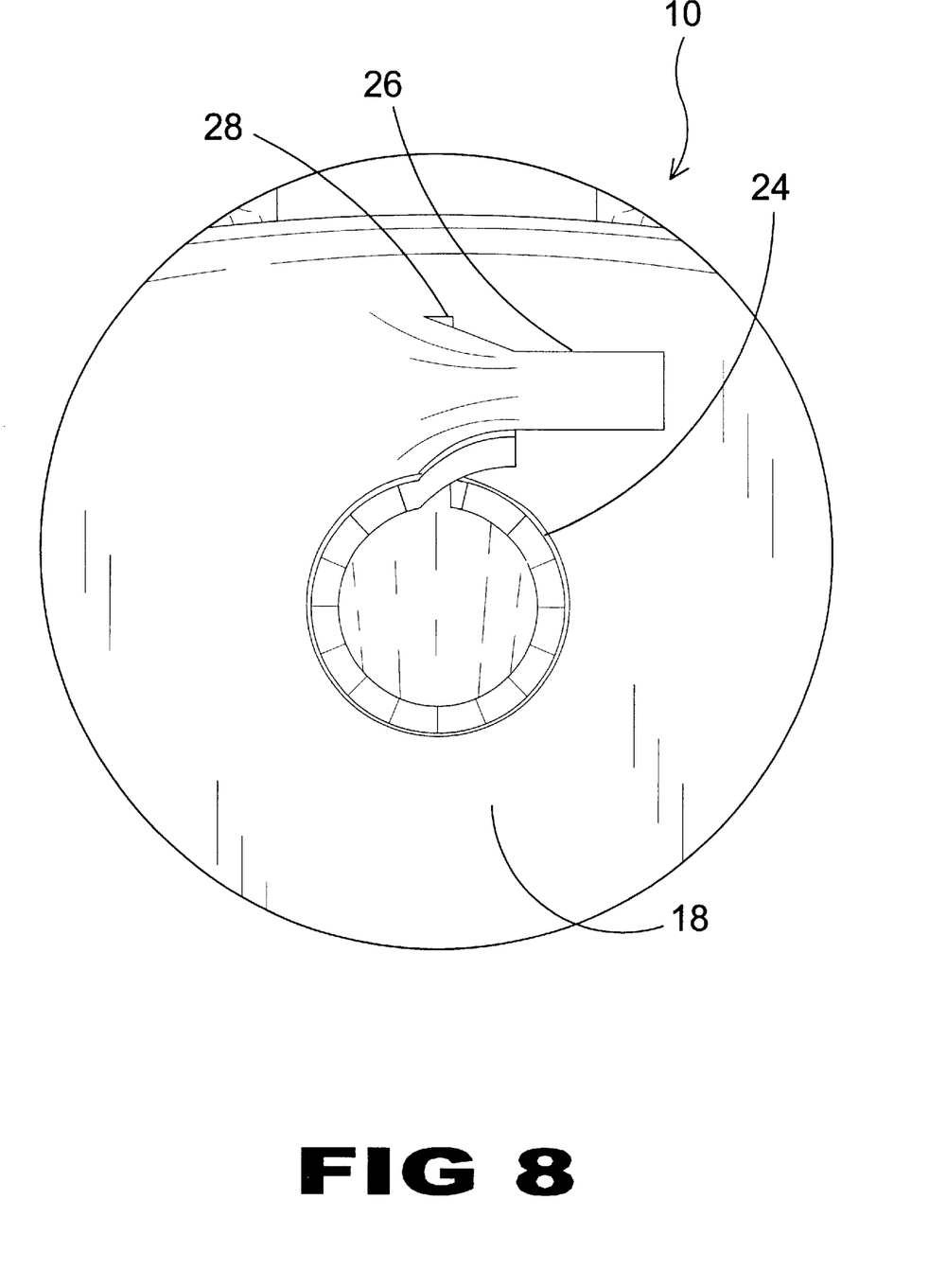
FIG. 8 is a back view of the present invention.

Turning to FIG. 8, shown therein is a back view of the present invention 10 showing the present invention with the sealing tab 26 pulled farther over the sides of the slit 28 to reduce the diameter of the elastic ring 24 so that it may accommodate different penis sizes. Bag 18 is also shown.

Figure 9:
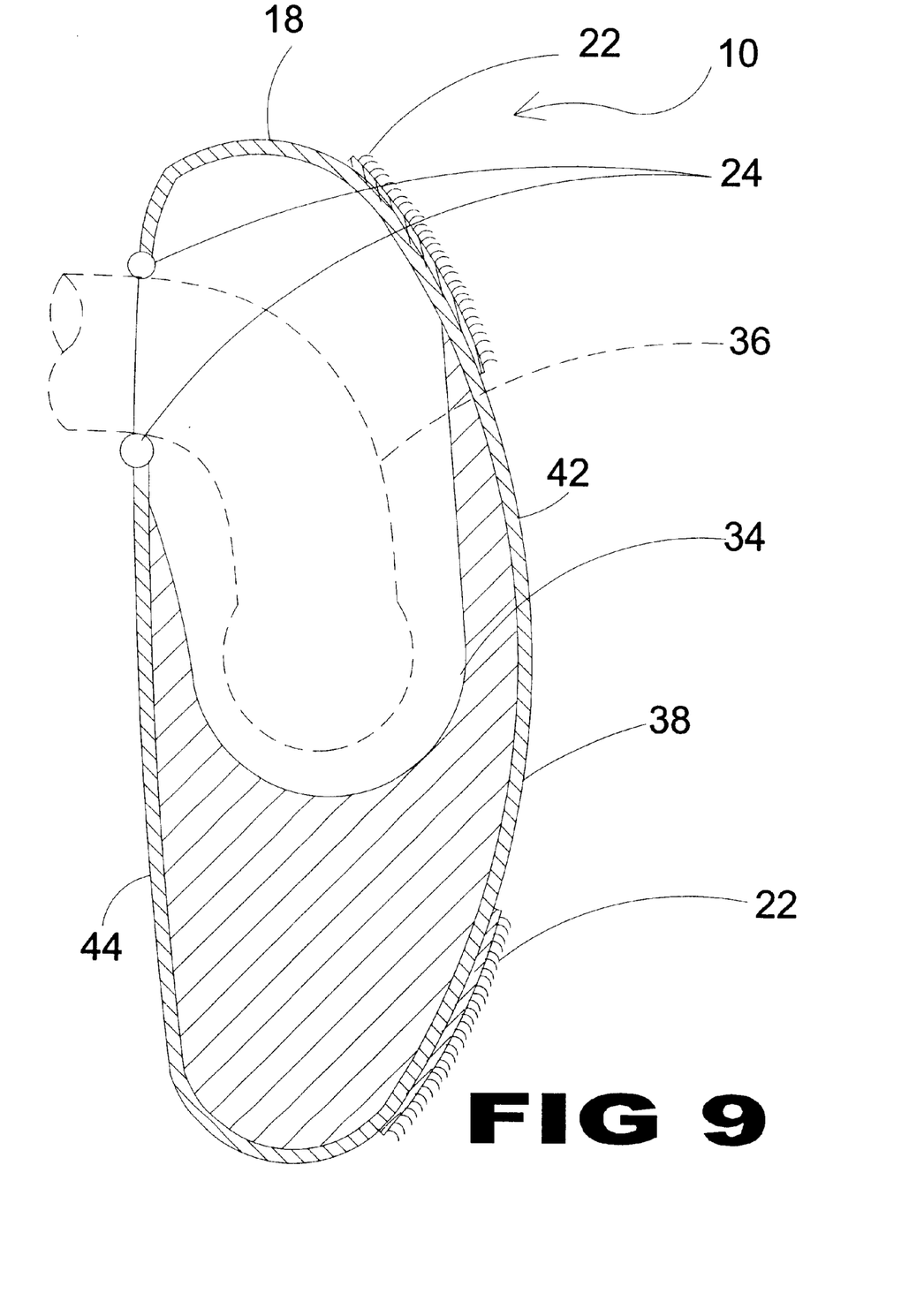
FIG. 9 is a cross section of the present invention.

Turning to FIG. 9, shown therein is a cross section of the present invention 10 showing the present invention having absorbent material 34 placed inside the disposable urinary bag 18 which has a front wall 42 and a rear wall 44. Also shown is a penis 36 inserted through the elastic ring 24 with the disposable urinary bag 18 providing enough room inside to avoid contact between the penis and the absorbent material. Also shown are an impermeable layer or sheet 38 and the means 22 for connecting the straps and belts.

I claim:

1. A male urinary apparatus for receiving a penis of a user, comprising:

a) a urinary bag for containing discharge of urine from the penis;

b) said urinary bag being shaped to fit within a crotch area of the user, said bag having an upper end, a lower end, a front side, and a rear side, and made from impermeable material that is leak-proof;

c) said bag having an opening in a central upper part of said rear side of said bag for receiving only said penis;

d) a ring disposed about said opening for encircling the penis;

e) means for adjusting the size of said ring for closely fitting said penis to prevent leakage of urine comprising a slit extending from said ring, said slit foldable back into folds, and a sealing tab attached to one of said folds for overlapping said folds, said tab having means for fastening said tab to said bag;

f) means for attaching said bag to the user, g) absorbent material disposed in said bag, said absorbent material having a cavity to receive the penis for absorbing urine;

h) said means for attaching said bag to the user comprising a waist strap adjustable in length, a pair of leg straps, and a pair of front straps; and i) said leg straps each having a first end and a second end, said first end being attached to said waist strap, and said second end having hook and loop material for attachment to said urinary bag, each of said front straps having a first end attached to said waist strap and a second end having hook and loop material for attachment to said urinary bag, said urinary bag having mating hook and loop material on the upper end of said front side for engagement with said front straps and mating hook and loop material on a lower end of said front side for engagement with said leg straps.

* * * * *